US008236763B2

(12) United States Patent
Lotersztajn et al.

(10) Patent No.: US 8,236,763 B2
(45) Date of Patent: Aug. 7, 2012

(54) USE OF ANTAGONISTS OF THE CB1 RECEPTOR FOR THE MANUFACTURE OF A COMPOSITION USEFUL FOR THE TREATMENT OF HEPATIC DISEASES

(75) Inventors: Sophie Lotersztajn, Paris (FR); Ariane Mallat, Paris (FR); Pascale Grenard, Bretigny (FR); Boris Julien, Paris (FR); Jeanne Tran Van Nhieu, St. Maur des Fosses (FR)

(73) Assignees: Inserm, Paris Cedex (FR); Sanofi-Aventis, Paris (FR)

( * ) Notice: Subject to any disclaimer, the term of this patent is extended or adjusted under 35 U.S.C. 154(b) by 305 days.

(21) Appl. No.: 10/598,736

(22) PCT Filed: Mar. 8, 2005

(86) PCT No.: PCT/EP2005/003285
§ 371 (c)(1),
(2), (4) Date: Jul. 19, 2007

(87) PCT Pub. No.: WO2005/084652
PCT Pub. Date: Sep. 15, 2005

(65) Prior Publication Data
US 2008/0214449 A1  Sep. 4, 2008

(30) Foreign Application Priority Data
Mar. 9, 2004  (EP) ..................................... 04290633

(51) Int. Cl.
*A61K 38/00* (2006.01)
(52) U.S. Cl. ........................... 514/12; 514/400; 514/326
(58) Field of Classification Search ................. 514/12, 514/400, 326
See application file for complete search history.

(56) References Cited

U.S. PATENT DOCUMENTS

| | | | | |
|---|---|---|---|---|
| 4,100,293 | A * | 7/1978 | Walser ............................ | 514/562 |
| 5,102,910 | A * | 4/1992 | Mittheiss et al. ............... | 514/494 |
| 5,492,891 | A * | 2/1996 | Skakkeb et al. ................. | 514/12 |
| 5,624,941 | A * | 4/1997 | Barth et al. ..................... | 514/326 |
| 5,939,429 | A | 8/1999 | Sanyal et al. | |
| 6,143,752 | A * | 11/2000 | Oren ............................... | 514/274 |
| 6,465,436 | B2 * | 10/2002 | Lukas et al. .................... | 514/27 |
| 6,632,647 | B2 * | 10/2003 | Hirth-Dietrich et al. ..... | 435/235.1 |
| 7,056,890 | B2 * | 6/2006 | Najarian ......................... | 514/23 |
| 7,091,216 | B2 * | 8/2006 | Toupence et al. .............. | 514/302 |
| 7,320,805 | B2 * | 1/2008 | Grenard et al. ................ | 424/725 |
| 2004/0034968 | A1 * | 2/2004 | Williams ......................... | 16/354 |
| 2004/0214804 | A1 * | 10/2004 | Gulve et al. .................... | 514/171 |

FOREIGN PATENT DOCUMENTS

| | | |
|---|---|---|
| WO | WO 03/063781 | 8/2003 |
| WO | WO 03/084930 | 10/2003 |
| WO | WO 03/084943 | 10/2003 |
| WO | WO 03/087037 | 10/2003 |
| WO | WO 2004/007551 A | 1/2004 |
| WO | WO 2004/058744 A | 7/2004 |
| WO | WO 2005/046689 A2 | 5/2005 |

OTHER PUBLICATIONS

Arnone et al., "Selective Inhibition of Sucrose and Ethanol Intake by SR 141716, an Antagonist of Central Cannabinoid (CB1) Receptors", Psychopharmacology, 1997, 132:104-106.*
Serra et al., "Blockage by the Cannabinoid CB1 Receptor Antagonist, SR 141716, of Alcohol Deprivation Effect in Alcohol-Preferring Rats", European Journal of Pharmacology, 443 (2002): 95-97.*
Racz et al., The Journal of Neuroscience, 2003, 23(6):2453-2458.*
Caprino, et al, "Alpha-SMA Expression in Hepatic Stellate Cells and Quantitative Analysis of Hepatic Fibrosis in Cirrhosis and in Recurrent Chronic Hepatitis After Liver Transplantation," Digestive and Liver Disease, vol. 37, pp. 349-356 (2005).*
P. Grenard et al., "Reduced Liver Fibrosis in CB1 Receptor Knockout Mice", Journal of Hepatology, vol. 40, p. 8 (Apr. 2004).
Batkai et al., Endocannabinoids Acting at Vascular CB1 Receptors Mediate the Vasodilated State in Advance Liver Cirrhosis:, Nature Medicine, Nature Publishing Co., vol. 7, No. 7, pp. 827-832 (Jul. 2001).
Gabbay et al., Treatment with an Endocannabinoid Antagonist Improves Neurological Function and Survival in an Animal Model of Fulminant Hepatic Failure:, Hepatogy, vol. 38, No. 4, p. 541A (Oct. 2003).
Julien et al., "Activation of cannabinoid receptors leads to apoptosis of human hepatic myofibroblasts", Hepatology, vol. 36, No. 4, p. 260A (Oct. 2002).

\* cited by examiner

*Primary Examiner* — Jeffrey S. Lundgren
*Assistant Examiner* — Ibrahim D Bori
(74) *Attorney, Agent, or Firm* — Scully, Scott, Murphy & Presser, P.C.

(57) ABSTRACT

The invention relates to the use of antagonists to the CB1 receptor for the preparation of a composition for the treatment of hepatic diseases and preferably to the use of N-piperidino-5-(4-chlorophenyl)-1-(2,4-dichlorophenyl)-4-methylpyrazole-3-carboxamide.

1 Claim, 4 Drawing Sheets

SEQUENCE LISTING

<160> NUMBER OF SEQ ID NOS: 12

<210> SEQ ID NO 1
<211> LENGTH: 472
<212> TYPE: PRT
<213> ORGANISM: Homo sapiens

<400> SEQUENCE: 1

```
Met Lys Ser Ile Leu Asp Gly Leu Ala Asp Thr Thr Phe Arg Thr Ile
1               5                   10                  15

Thr Thr Asp Leu Leu Tyr Val Gly Ser Asn Asp Ile Gln Tyr Glu Asp
                20                  25                  30

Ile Lys Gly Asp Met Ala Ser Lys Leu Gly Tyr Phe Pro Gln Lys Phe
            35                  40                  45

Pro Leu Thr Ser Phe Arg Gly Ser Pro Phe Gln Glu Lys Met Thr Ala
        50                  55                  60

Gly Asp Asn Pro Gln Leu Val Pro Ala Asp Gln Val Asn Ile Thr Glu
65                  70                  75                  80

Phe Tyr Asn Lys Ser Leu Ser Ser Phe Lys Glu Asn Glu Glu Asn Ile
                85                  90                  95

Gln Cys Gly Glu Asn Phe Met Asp Ile Glu Cys Phe Met Val Leu Asn
            100                 105                 110

Pro Ser Gln Gln Leu Ala Ile Ala Val Leu Ser Leu Thr Leu Gly Thr
        115                 120                 125

Phe Thr Val Leu Glu Asn Leu Leu Val Leu Cys Val Ile Leu His Ser
    130                 135                 140

Arg Ser Leu Arg Cys Arg Pro Ser Tyr His Phe Ile Gly Ser Leu Ala
145                 150                 155                 160

Val Ala Asp Leu Leu Gly Ser Val Ile Phe Val Tyr Ser Phe Ile Asp
                165                 170                 175

Phe His Val Phe His Arg Lys Asp Ser Arg Asn Val Phe Leu Phe Lys
            180                 185                 190

Leu Gly Gly Val Thr Ala Ser Phe Thr Ala Ser Val Gly Ser Leu Phe
        195                 200                 205

Leu Thr Ala Ile Asp Arg Tyr Ile Ser Ile His Arg Pro Leu Ala Tyr
    210                 215                 220

Lys Arg Ile Val Thr Arg Pro Lys Ala Val Val Ala Phe Cys Leu Met
225                 230                 235                 240

Trp Thr Ile Ala Ile Val Ile Ala Val Leu Pro Leu Leu Gly Trp Asn
                245                 250                 255

Cys Glu Lys Leu Gln Ser Val Cys Ser Asp Ile Phe Pro His Ile Asp
            260                 265                 270

Glu Thr Tyr Leu Met Phe Trp Ile Gly Val Thr Ser Val Leu Leu Leu
        275                 280                 285

Phe Ile Val Tyr Ala Tyr Met Tyr Ile Leu Trp Lys Ala His Ser His
    290                 295                 300

Ala Val Arg Met Ile Gln Arg Gly Thr Gln Lys Ser Ile Ile Ile His
305                 310                 315                 320

Thr Ser Glu Asp Gly Lys Val Gln Val Thr Arg Pro Asp Gln Ala Arg
                325                 330                 335

Met Asp Ile Arg Leu Ala Lys Thr Leu Val Leu Ile Leu Val Val Leu
            340                 345                 350
```

```
Ile Ile Cys Trp Gly Pro Leu Leu Ala Ile Met Val Tyr Asp Val Phe
        355                 360                 365

Gly Lys Met Asn Lys Leu Ile Lys Thr Val Phe Ala Phe Cys Ser Met
        370                 375                 380

Leu Cys Leu Leu Asn Ser Thr Val Asn Pro Ile Ile Tyr Ala Leu Arg
385                 390                 395                 400

Ser Lys Asp Leu Arg His Ala Phe Arg Ser Met Phe Pro Ser Cys Glu
                405                 410                 415

Gly Thr Ala Gln Pro Leu Asp Asn Ser Met Gly Asp Ser Asp Cys Leu
            420                 425                 430

His Lys His Ala Asn Asn Ala Ala Ser Val His Arg Ala Ala Glu Ser
        435                 440                 445

Cys Ile Lys Ser Thr Val Lys Ile Ala Lys Val Thr Met Ser Val Ser
    450                 455                 460

Thr Asp Thr Ser Ala Glu Ala Leu
465                 470

<210> SEQ ID NO 2
<211> LENGTH: 411
<212> TYPE: PRT
<213> ORGANISM: Homo sapiens

<400> SEQUENCE: 2

Met Ala Leu Gln Ile Pro Pro Ser Ala Pro Ser Pro Leu Thr Ser Cys
1               5                   10                  15

Thr Trp Ala Gln Met Thr Phe Ser Thr Lys Ser Lys Glu Asn Glu
        20                  25                  30

Glu Asn Ile Gln Cys Gly Glu Asn Phe Met Asp Ile Glu Cys Phe Met
            35                  40                  45

Val Leu Asn Pro Ser Gln Gln Leu Ala Ile Ala Val Leu Ser Leu Thr
50                  55                  60

Leu Gly Thr Phe Thr Val Leu Glu Asn Leu Leu Val Leu Cys Val Ile
65                  70                  75                  80

Leu His Ser Arg Ser Leu Arg Cys Arg Pro Ser Tyr His Phe Ile Gly
                85                  90                  95

Ser Leu Ala Val Ala Asp Leu Leu Gly Ser Val Ile Phe Val Tyr Ser
            100                 105                 110

Phe Ile Asp Phe His Val Phe His Arg Lys Asp Ser Arg Asn Val Phe
        115                 120                 125

Leu Phe Lys Leu Gly Gly Val Thr Ala Ser Phe Thr Ala Ser Val Gly
    130                 135                 140

Ser Leu Phe Leu Thr Ala Ile Asp Arg Tyr Ile Ser Ile His Arg Pro
145                 150                 155                 160

Leu Ala Tyr Lys Arg Ile Val Thr Arg Pro Lys Ala Val Val Ala Phe
                165                 170                 175

Cys Leu Met Trp Thr Ile Ala Ile Val Ile Ala Val Leu Pro Leu Leu
            180                 185                 190

Gly Trp Asn Cys Glu Lys Leu Gln Ser Val Cys Ser Asp Ile Phe Pro
        195                 200                 205

His Ile Asp Glu Thr Tyr Leu Met Phe Trp Ile Gly Val Thr Ser Val
    210                 215                 220

Leu Leu Leu Phe Ile Val Tyr Ala Tyr Met Tyr Ile Leu Trp Lys Ala
225                 230                 235                 240

His Ser His Ala Val Arg Met Ile Gln Arg Gly Thr Gln Lys Ser Ile
                245                 250                 255
```

-continued

```
Ile Ile His Thr Ser Glu Asp Gly Lys Val Gln Val Thr Arg Pro Asp
        260                 265                 270

Gln Ala Arg Met Asp Ile Arg Leu Ala Lys Thr Leu Val Leu Ile Leu
        275                 280                 285

Val Val Leu Ile Ile Cys Trp Gly Pro Leu Leu Ala Ile Met Val Tyr
        290                 295                 300

Asp Val Phe Gly Lys Met Asn Lys Leu Ile Lys Thr Val Phe Ala Phe
305                 310                 315                 320

Cys Ser Met Leu Cys Leu Leu Asn Ser Thr Val Asn Pro Ile Ile Tyr
                325                 330                 335

Ala Leu Arg Ser Lys Asp Leu Arg His Ala Phe Arg Ser Met Phe Pro
                340                 345                 350

Ser Cys Glu Gly Thr Ala Gln Pro Leu Asp Asn Ser Met Gly Asp Ser
                355                 360                 365

Asp Cys Leu His Lys His Ala Asn Asn Ala Ala Ser Val His Arg Ala
                370                 375                 380

Ala Glu Ser Cys Ile Lys Ser Thr Val Lys Ile Ala Lys Val Thr Met
385                 390                 395                 400

Ser Val Ser Thr Asp Thr Ser Ala Glu Ala Leu
                405                 410

<210> SEQ ID NO 3
<211> LENGTH: 20
<212> TYPE: PRT
<213> ORGANISM: Homo sapiens

<400> SEQUENCE: 3

Phe Arg Thr Ile Thr Thr Asp Leu Leu Tyr Val Gly Ser Asn Asp Ile
1               5                   10                  15

Gln Tyr Glu Asp
            20

<210> SEQ ID NO 4
<211> LENGTH: 23
<212> TYPE: PRT
<213> ORGANISM: Homo sapiens

<400> SEQUENCE: 4

Asp Met Ala Ser Lys Leu Gly Tyr Phe Pro Gln Lys Phe Pro Leu Thr
1               5                   10                  15

Ser Phe Arg Gly Ser Pro Phe
            20

<210> SEQ ID NO 5
<211> LENGTH: 20
<212> TYPE: PRT
<213> ORGANISM: Homo sapiens

<400> SEQUENCE: 5

Thr Glu Phe Tyr Asn Lys Ser Leu Ser Ser Phe Lys Glu Asn Glu Glu
1               5                   10                  15

Asn Ile Gln Cys
            20

<210> SEQ ID NO 6
<211> LENGTH: 20
<212> TYPE: PRT
<213> ORGANISM: Homo sapiens

<400> SEQUENCE: 6
```

```
Arg Met Ile Gln Arg Gly Thr Gln Lys Ser Ile Ile Ile His Thr Ser
1               5                   10                  15

Glu Asp Gly Lys
            20

<210> SEQ ID NO 7
<211> LENGTH: 12
<212> TYPE: PRT
<213> ORGANISM: Homo sapiens

<400> SEQUENCE: 7

Val Tyr Asp Val Phe Gly Lys Met Asn Lys Leu Ile
1               5                   10

<210> SEQ ID NO 8
<211> LENGTH: 20
<212> TYPE: PRT
<213> ORGANISM: Homo sapiens

<400> SEQUENCE: 8

His Lys His Ala Asn Asn Ala Ala Ser Val His Arg Ala Ala Glu Ser
1               5                   10                  15

Cys Ile Lys Ser
            20

<210> SEQ ID NO 9
<211> LENGTH: 20
<212> TYPE: PRT
<213> ORGANISM: Homo sapiens

<400> SEQUENCE: 9

His Lys His Ala Asn Asn Thr Ala Ser Met His Arg Ala Ala Glu Ser
1               5                   10                  15

Cys Ile Lys Ser
            20

<210> SEQ ID NO 10
<211> LENGTH: 31
<212> TYPE: DNA
<213> ORGANISM: Artificial Sequence
<220> FEATURE:
<223> OTHER INFORMATION: CB1 sense primer

<400> SEQUENCE: 10
tttggctaca caattggaag tctaagaacc c                              31

<210> SEQ ID NO 11
<211> LENGTH: 28
<212> TYPE: DNA
<213> ORGANISM: Artificial Sequence
<220> FEATURE:
<223> OTHER INFORMATION: CB1 antisense primer

<400> SEQUENCE: 11
gcacacattg acacgtatcc actgcttg                                  28
```

```
<210> SEQ ID NO 12
<211> LENGTH: 30
<212> TYPE: DNA
<213> ORGANISM: Artificial Sequence
<220> FEATURE:
<223> OTHER INFORMATION: CB1 oligonucleotide probe

<400> SEQUENCE: 12
cctgtgagat gtgtatcagt gtttatgtgc                                     30
```

USE OF ANTAGONISTS OF THE CB1 RECEPTOR FOR THE MANUFACTURE OF A COMPOSITION USEFUL FOR THE TREATMENT OF HEPATIC DISEASES

FIELD OF THE INVENTION

The invention relates to a new use for antagonists to the CB1 receptor for the manufacture of a composition useful for the treatment of hepatic diseases.

BACKGROUND OF THE INVENTION

Liver fibrosis is the common response to chronic liver injury, ultimately leading to cirrhosis and its complications, portal hypertension, liver failure and hepatocellular carcinoma. The fibrogenic process is consecutive to intense proliferation and accumulation of hepatic myofibroblasts that synthesize fibrosis components and inhibitors of matrix degradation (Friedman, S. L., *J Biol Chem* 275, 2247-50 (2000)).

Cannabis Sativa contains over sixty compounds, the most active of which is (−) $\Delta^9$-tetrahydrocannabinol (THC). Endogenous natural cannabinoids have also been characterized, anandamide and 2-arachidonyl glycerol, which are arachidonic acid-derived lipids (Piomelli, D et al, *Trends Phamacol Sci* 21, 218-24. (2000)). Cannabinoids bind to two G protein-coupled receptors, CB1 and CB2, that equally bind THC (Pertwee, R. G., *Curr Med Chem* 6, 635-64. (1999)). CB1 is thus one of the two known cellular receptors for cannabinoids. This receptor being a G protein-coupled transmembrane receptor is known to be expressed in brain and blood vessels (Pertwee, R. G., *Curr Med Chem* 6, 635-64 (1999)) but not in hepatocytes (Guzman, M & Sanchez, C., *Life Sci* 65, 657-64 (1999)). CB1 mediates the psychoactive effects of *cannabis*. In contrast, CB2 receptors are mainly expressed in the immune system and are devoid of psychoactive effects (Friedman, S. L., *J Biol Chem* 275, 2247-50 (2000)). In addition to their psychotropic effects, cannabinoids display analgesic, antiemetic and orexigenic central effects (Harrold, J. A. & Williams, G. *Br J Nutr* 90, 729-34 (2003)). Moreover, cannabinoids also elicit anti-inflammatory and vasorelaxing properties (Kumar, R. N., Chambers, W. A. & Pertwee, *Anaesthesia* 56, 1059-68. (2001)). Several studies also suggest that cannabinoids may be potential antitumoral agents, owing to their ability to induce the regression of various types of experimental tumors, including glioma or skin tumors. These antitumoral effects are mainly attributed to their antiproliferative and apoptotic properties (Bifulco, M. et al., *Faseb J* 29, 29 (2001); Casanova, M. L. et al., *J Clin Invest* 111, 43-50. (2003); Sanchez, C. et al., *Cancer Res* 61, 5784-9. (2001)).

There are only few data concerning the hepatic action of cannabinoids. CB1 and CB2 receptors are not expressed in hepatocytes (Guzman, M. & Sanchez, C. *Life Sci* 65, 657-64 (1999)). However, CB1 receptors are present in endothelial cells isolated from hepatic arteries, and their expression increase during cirrhosis (Batkai, S. et al. *Nat Med* 7, 827-32. (2001)).

Two isoforms of the receptor CB1 have been isolated: a long isoform (corresponding to SEQ ID NO:1) and a shorter one truncated in the NH2 terminal part corresponding to a splice variant (corresponding to SEQ ID NO:2), which differ in their affinity for their ligands (Shire et al., *J Biol Chem*, (1995); Rinaldi-Carmona et al, *J Pharmacol Exp Ther* (1996)). There also exist 5 single nucleotide polymorphisms in the coding region of the CB1 receptor gene. Of these only three result in single amino acid changes to the CB1 receptor (these being, in SEQ ID NO:1, a Phenylalanine to Leucine substitution at position 200, an Isoleucine to Valine substitution at position 216 and a Valine to Alanine substitution at position 246 and the corresponding positions in SEQ ID NO:2). A consensus 7-domains sequence for the CB1 receptor exists which is strongly conserved in vertebrates but does not appear in other cannabinoid receptors (Attwood, T. K. and Findlay, J. B. C., *Protein Eng* 7(2) 195-203 (1994), Attwood, T. K. and Findlay, J. B. C., 7TM, Volume 2 Eds G. Vriend and B. Bywater, (1993), Birnbaumer, L., *Ann. Rev Pharmacol Toxicol*, 30, 675-705 (1990), Casey, P. J. and Gilman, A. G., *J. Biol. Chem.* 263(6) 2577-2580 (1988), 5. Attwood, T. K. and Findlay, J. B. C, *Protein Eng* 6(2) 167-176 (1993), Watson, S, and Arkinsall, S, *In The G Protein-Linked Receptor Factsbook*, Academic press, 1994, PP 80-83). That consensus amino acid sequence comprises the 7 protein domains of SEQ ID NO:3 to SEQ ID NO:9.

Antagonists to the receptor CB1, which include reverse or inverse agonists, have been previously described. These include the substituted amides described in WO03/077847, the substituted aryl amides described in WO03/087037, the substituted imidazoles described in WO03/063781, bicyclic amides described in WO03/086288, the terphenyl derivatives described in WO 03/084943, the N-piperidono-3-pyrazole-carboxamide and N-piperidino-5-(4-chlorophenyl)-1-(2,4-dichlorophenyl)-4-methylpyrazole-3-carboxamide described in EP-B-656354, the aryl-benzo[b]thiophene and benzo[b]furan compounds respectively described in U.S. Pat. No. 5,596,106 and U.S. Pat. No. 5,747,524, the azetidine derivatives described in FR2805817, 3-amino-azetidine described in FR2805810, or the 3-Substituted or 3,3-disubstituted 1-(di-((hetero)aryl)-methyl)-azetidine derivatives described in FR2805818. These documents are incorporated herein by reference. Other antagonists are commercially available such as N-(piperidin-1-yl)-1-(2,4-dichlorophenyl)-5-(4-iodophenyl)-4-methyl-1H-pyrazole-3-carboxamide, known commercially as AM251 and the compound known as LY-320135.

Uses of these CB1 receptor antagonists are known for the treatment of sexual dysfunction (patent application WO 03/082256), or diarrhoea (patent application WO 01/85092), or neuro-inflammatory diseases or substance abuse disorders, obesity, asthma, constipation (patent application WO 03/077847).

Documents U.S. Pat. No. 5,939,429, WO 03/077847, WO 03/084930, WO 03/084943, WO 03/063781 and WO 03/087037 disclose that CB1 antagonists can reverse the systemic hemodynamic alterations in rats with cirrhotic portal hypertension.

SUMMARY OF THE INVENTION

However, the documents above mentioned never disclose that CB1 antagonists can reduce fibrogenesis in hepatic diseases of any etiology (alcoholic, viral, toxic). Moreover, there is no known involvement of CB1 receptors or effects of CB1 antagonists in non-alcoholic steatohepatitis and liver carcinogenesis.

The inventors now surprisingly demonstrate that CB1 antagonists have potent anti-fibrotic properties in the liver which can be used for the treatment of hepatic diseases and preferably hepatic diseases which result in hepatic fibrosis.

Accordingly, the present invention, based on the finding that inactivation of CB1 receptors can reduce liver fibrogenesis associated with liver injury or disease, provides a variety of methods and compositions for treating hepatic diseases and preferably hepatic diseases which result in hepatic fibrosis. The invention thus relates to:
1. Use of an antagonist of the CB1 receptor in the manufacture of a composition for the treatment of hepatic diseases.
2. Use according to item 1 wherein the antagonist of the CB1 receptor is a specific antagonist of the CB1 receptor.
3. Use according to items 1 or 2 wherein the hepatic disease results in hepatic fibrosis.
4. Use according to items 1 to 3 wherein the hepatic disease is alcoholic liver cirrhosis.
5. Use according to items 1 to 3 wherein the hepatic disease is chronic viral hepatitis.
6. Use according to items 1 to 3 wherein the hepatic disease is non-alcoholic steatohepatitis.
7. Use according to items 1 to 3 wherein the hepatic disease is primary liver cancer.
8. Use according to items 1 to 7 wherein the antagonist is a compound of the formula II or one of its pharmaceutically acceptable salt, in which $g_2$, $g_3$, $g_4$, $g_5$ and $g_6$ and $w_2$, $w_3$, $w_4$, $w_5$ and $w_6$ are identical or different and are independently hydrogen, a chlorine or bromine atom, a $(C_1-C_3)$ alkyl, a $(C_1-C_3)$ alkoxy, a trifluoromethyl or a nitro group and $g_4$ is optionally a phenyl group; $R_4$ is hydrogen or a $(C_1-C_3)$ alkyl; X is either a direct bond or a group —$(CH_2)_x$—$N(R_3)$—, in which $R_3$ is hydrogen or a $(C_1-C_3)$ alkyl and x is zero or one; R is: a group —$NR_1R_2$ in which $R_1$ and $R_2$ are independently a $(C_1-C_6)$-alkyl; an non-aromatic $(C_3-C_{15})$ carbocyclic radical which is optionally substituted, said substituent(s) being other than a substituted carbonyl; an amino $(C_1-C_4)$ alkyl group in which the amino is optionally disubstituted by a $(C_1-C_3)$ alkyl; a cycloalkyl $(C_1-C_3)$ alkyl in which the cycloalkyl is $C_3-C_{12}$; a phenyl which is unsubstituted or monosubstituted or polysubstituted by a halogen, by a $(C_1-C_5)$ alkyl or by a $(C_1-C_5)$ alkoxy; a phenyl $(C_1-C_3)$ alkyl; a diphenyl $(C_1-C_3)$ alkyl; a naphthyl; an anthracenyl; a saturated 5- to 8-membered heterocyclic radical which is unsubstituted or substituted by a $(C_1-C_3)$ alkyl, by a hydroxyl or by a benzyl; a 1-adamantylmethyl; an aromatic heterocycle which is unsubstituted or monosubstituted or polysubstituted by a halogen, by a $(C_1-C_5)$ alkyl or by a $(C_1-C_5)$ alkoxy; a $(C_1-C_3)$ alkyl which is substituted by an aromatic heterocycle which is unsubstituted or monosubstituted or polysubstituted by a halogen, by a $(C_1-C_5)$ alkyl or by a $(C_1-C_5)$ alkoxy; or else $R_1$ is hydrogen and $R_2$ is as defined above; or else $R_1$ and $R_2$ form a saturated 5- to 8-membered heterocyclic radical with the nitrogen atom to which they are bonded, said heterocyclic radical being other than morpholine when $w_2$, $w_3$, $w_4$, $w_5$, $w_6$, $g_2$, $g_3$, $g_4$, $g_5$ and $g_6$ are all hydrogen; a group $R_2$ as defined above when X is —$(CH_2)_xN(R_3)$—; a group $R_5$ when X is a direct bond, $R_5$ being a $(C_1-C_3)$ alkyl; a $(C_3-C_{12})$ cycloalkyl which is unsubstituted or substituted by a $(C_1-C_5)$ alkyl; a phenyl $(C_1-C_3)$ alkyl which is unsubstituted or substituted by a halogen or by a $(C_1-C_5)$ alkyl; a cycloalkyl $(C_1-C_3)$ alkyl in which the cycloalkyl is $C_3-C_{12}$ and is unsubstituted or substituted by a $(C_1-C_5)$ alkyl; or a 2-norbornylmethyl.

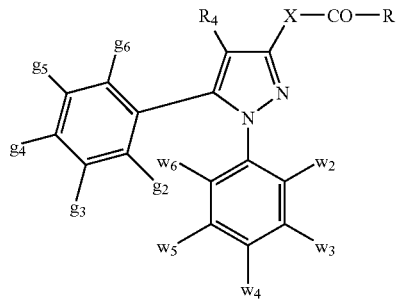

(II)

9. Use according to items 1 to 7 wherein the antagonist is N-piperidono-3-pyrazolecarboxamide or one of its pharmaceutically acceptable salt.
10. Use according to items 1 to 7 wherein the antagonist is N-piperidino-5-(4-bromophenyl)-1-(2,4-dichlorophenyl)-4-ethylpyrazole-3-carboxamide or one of its pharmaceutically acceptable salt.
11. Use according to items 1 to 7 wherein the antagonist is N-piperidino-5-(4-chlorophenyl)-1-(2,4-dichlorophenyl)-4-methylpyrazole-3-carboxamide or one of its pharmaceutically acceptable salt.
12. Use according to any of the preceding items wherein the CB1 receptor is selected from the group consisting of:
   a) a protein having an amino acid sequence comprising SEQ ID NO:1 or a portion of SEQ ID NO:1, having the biological function of a G protein-coupled cellular receptor, capable of binding THC and transducing a cellular signal;
   b) a protein having an amino acid sequence comprising SEQ ID NO:2 or a portion of SEQ ID NO:2, having the biological function of a G protein-coupled cellular receptor, capable of binding THC and transducing a cellular signal;
   c) an allele of the protein having the amino acid sequence of SEQ ID NO:1 or SEQ ID NO:2, having the biological function of a G protein-coupled cellular receptor, capable of binding THC and transducing a cellular signal;
   d) a protein having the amino acid sequence of SEQ ID NO:1 with a Phenylalanine to Leucine substitution at position 200; and/or an Isoleucine to Valine substitution at position 216; and/or a Valine to Alanine substitution at position 246;
   e) a protein having the amino acid sequence of SEQ ID NO:2 with a Phenylalanine to Leucine substitution at position 139; and/or an Isoleucine to Valine substitution at position 155; and/or a Valine to Alanine substitution at position 185; and
   f) a protein comprising the amino acid sequences of SEQ ID NO:3, SEQ ID NO:4, SEQ ID NO:5, SEQ ID NO:6, SEQ ID NO:7, SEQ ID NO:8 and SEQ ID NO:9 or amino acid sequences 80% homologous to these, said protein having the biological function of a G protein-coupled cellular receptor, capable of binding THC and transducing a cellular signal.
13. Use according to items 1 to 11 wherein the CB1 receptor is a protein having a homology at the amino acid level with SEQ ID NO:1 of at least 45%, having the biological function of a G protein-coupled cellular receptor, capable of binding THC and transducing a cellular signal.

14. Use according to the preceding item wherein the homology is at least 60%, preferably 70%, more preferably 80%, even more preferably 90% and more preferably 95%.
15. Use according to any of the preceding items wherein the daily dosage of CB1 receptor antagonist is from 0.01 mg to 500 mg, preferably from 1 mg to 100 mg.
16. Use of a nucleic acid sequence coding for a protein comprising SEQ ID NO:1 or SEQ ID NO:2 or a portion of SEQ ID NO:1 or a portion of SEQ ID NO:2, for the preparation of a composition for the treatment of hepatic diseases by the downregulation or suppression of the CB1 receptor.
17. A method of treatment of hepatic diseases in a mammal comprising the administration of a therapeutically effective amount of at least one CB1 receptor antagonist to a mammal in need thereof.
18. A method of treatment of hepatic diseases according to item 17 wherein the CB1 receptor antagonist is a compound of the formula II or one of its pharmaceutically acceptable salt, in which $g_2$, $g_3$, $g_4$, $g_5$ and $g_6$ and $w_2$, $w_3$, $w_4$, $w_5$ and $w_6$ are identical or different and are independently hydrogen, a chlorine or bromine atom, a ($C_1$-$C_3$) alkyl, a ($C_1$-$C_3$) alkoxy, a trifluoromethyl or a nitro group and $g_4$ is optionally a phenyl group; $R_4$ is hydrogen or a ($C_1$-$C_3$) alkyl; X is either a direct bond or a group —$(CH_2)_x$—$N(R_3)$—, in which $R_3$ is hydrogen or a ($C_1$-$C_3$) alkyl and x is zero or one; R is: a group —$NR_1R_2$ in which $R_1$ and $R_2$ are independently a ($C_1$-$C_6$)-alkyl; an non-aromatic ($C_3$-$C_{15}$) carbocyclic radical which is optionally substituted, said substituent(s) being other than a substituted carbonyl; an amino ($C_1$-$C_4$) alkyl group in which the amino is optionally disubstituted by a ($C_1$-$C_3$) alkyl; a cycloalkyl ($C_1$-$C_3$) alkyl in which the cycloalkyl is $C_3$-$C_{12}$; a phenyl which is unsubstituted or monosubstituted or polysubstituted by a halogen, by a ($C_1$-$C_5$) alkyl or by a ($C_1$-$C_5$) alkoxy; a phenyl ($C_1$-$C_3$) alkyl; a diphenyl ($C_1$-$C_3$) alkyl; a naphthyl; an anthracenyl; a saturated 5- to 8-membered heterocyclic radical which is unsubstituted or substituted by a ($C_1$-$C_3$) alkyl, by a hydroxyl or by a benzyl; a 1-adamantylmethyl; an aromatic heterocycle which is unsubstituted or monosubstituted or polysubstituted by a halogen, by a ($C_1$-$C_5$) alkyl or by a ($C_1$-$C_5$) alkoxy; a ($C_1$-$C_3$) alkyl which is substituted by an aromatic heterocycle which is unsubstituted or monosubstituted or polysubstituted by a halogen, by a ($C_1$-$C_5$) alkyl or by a ($C_1$-$C_5$) alkoxy; or else $R_1$ is hydrogen and $R_2$ is as defined above; or else $R_1$ and $R_2$ form a saturated 5- to 8-membered heterocyclic radical with the nitrogen atom to which they are bonded, said heterocyclic radical being other than morpholine when $w_2$, $w_3$, $w_4$, $w_5$, $w_6$, $g_2$, $g_3$, $g_4$, $g_5$ and $g_6$ are all hydrogen; a group $R_2$ as defined above when X is —$(CH_2)_xN(R_3)$—; a group $R_5$ when X is a direct bond, $R_5$ being a ($C_1$-$C_3$) alkyl; a ($C_3$-$C_{12}$) cycloalkyl which is unsubstituted or substituted by a ($C_1$-$C_5$) alkyl; a phenyl ($C_1$-$C_3$) alkyl which is unsubstituted or substituted by a halogen or by a ($C_1$-$C_5$) alkoxy; a cycloalkyl ($C_1$-$C_3$) alkyl in which the cycloalkyl is $C_3$-$C_{12}$ and is unsubstituted or substituted by a ($C_1$-$C_5$) alkyl; or a 2-norbornylmethyl.

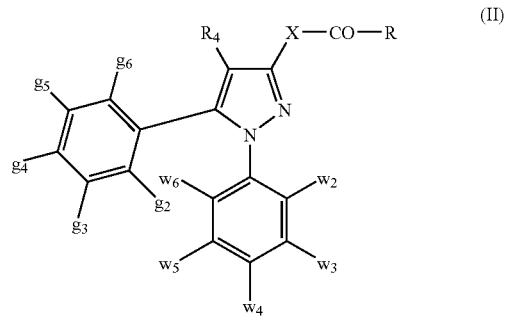

19. A method of treatment of hepatic diseases according to item 17 wherein the CB1 receptor antagonist is N-piperidono-3-pyrazolecarboxamide or one of its pharmaceutically acceptable salt.
20. A method of treatment of hepatic diseases according to item 17 wherein the CB1 receptor antagonist is N-piperidino-5-(4-bromophenyl)-1-(2,4-dichlorophenyl)-4-ethylpyrazole-3-carboxamide or one of its pharmaceutically acceptable salt.
21. A method of treatment of hepatic diseases according to item 17 wherein the CB1 receptor antagonist is N-piperidino-5-(4-chlorophenyl)-1-(2,4-dichlorophenyl)-4-methylpyrazole-3-carboxamide or one of its pharmaceutically acceptable salt.
22. A method of treatment of hepatic diseases according to items 17 to 21 wherein the hepatic disease is liver fibrosis.
23. A method of treatment of hepatic diseases according to items 17 to 21 wherein the hepatic disease is alcoholic liver cirrhosis.
24. A method of treatment of hepatic diseases according to items 17 to 21 wherein the hepatic disease is chronic viral hepatitis.
25. A method of treatment of hepatic diseases according to items 17 to 21 wherein the hepatic disease is non-alcoholic steatohepatitis.
26. A method of treatment of hepatic diseases according to items 17 to 21 wherein the hepatic disease is primary liver cancer.
27. A method of treatment of hepatic diseases according to items 17 to 26 wherein the daily dosage of CB1 receptor antagonist is from 0.01 mg to 500 mg, preferably from 1 mg to 100 mg.

The hepatic TGFβ-1 production was measured (statistical significance is p<0.05). For the assessment of smooth muscle alpha actin, staining was quantified on 4-5 liver tissue section per animal (statistical significance is p<0.05).

Figure 2:
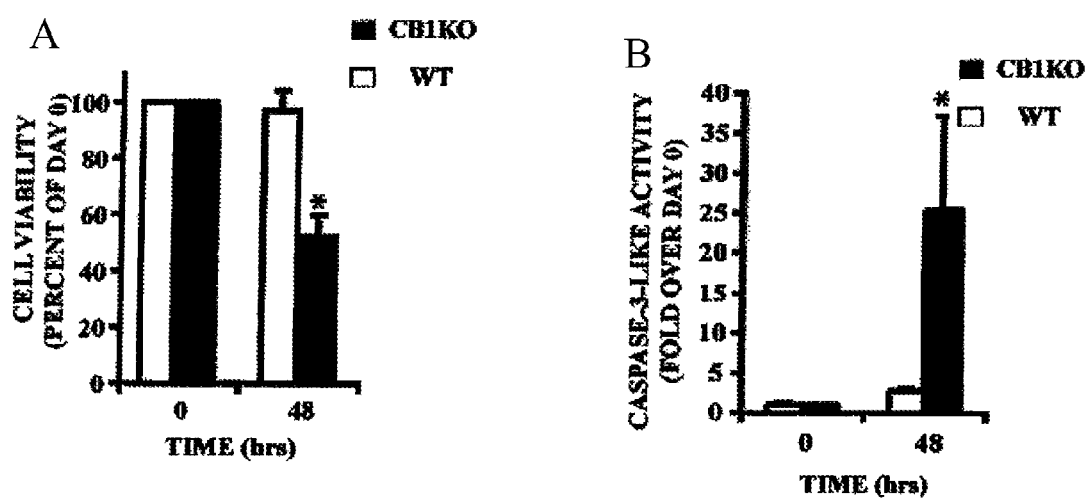

FIG. 2: Histograms showing respectively the hepatic myofibroblast viability (panel A) and Caspase-3-like activity (panel B) initially and after 48 hours following serum deprivation both in wild type mice (shown as WT) and CB1 deficient mice (shown as CB1KO). Apoptosis was induced by serum deprivation for 48 h. Results for the hepatic myofibroblast viability are expressed as mean percentage of cells surviving ±SEM, from 6-9 experiments obtained from cells isolated from livers of 3 WT and 2 CB1 −/− mice (statistical significance p is inferior to 0.05 for CB1 −/−). Results for Caspase-3-like activity are expressed as fold over activity measured at day 0 (the mean ±SEM was obtained from 6-9 experiments obtained from cells isolated from livers of 3 WT and 3 CB1 −/− mice). Statistically p is inferior to 0.05.

Figure 3:
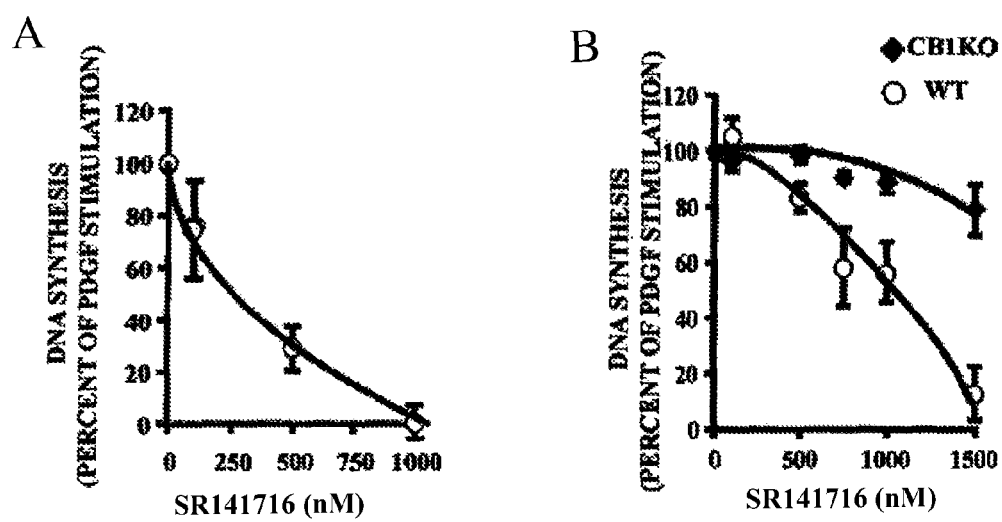

FIG. 3: Plots showing the effect of increasing amounts of CB1 antagonist SR141716 on DNA synthesis in human hepatic myofibroblast (panel A) and on wild type mice (shown as WT) and CB1 deficient mice (shown as CB1KO) (panel B). The DNA synthesis is expressed as a percentage of DNA synthesis in cells treated with the vehicle of SR 141716 and plotted against increasing concentrations of SR 141716 in nM. Human hepatic myofibroblast cells were stimulated for 30 h with varying concentrations of the CB1 receptor antagonist SR 141716, in the presence of 20 ng/ml of PDGF-BB. [$^3$H] Thymidine incorporation into DNA was measured as mean ±SEM, from 3-6 experiments and is expressed as percent of control (p is inferior to 0.05). Error bars are shown on the plot. Mouse hepatic myofibroblast (from wild type mice shown on the plot as circles and CB1 deficient mice shown as diamonds) were stimulated for 30 h with varying concentrations of the CB1 receptor antagonist SR 141716, in the presence of 20 ng/ml of PDGF-BB. [$^3$H] Thymidine incorporation into DNA was measured as mean ±SEM, from 3-6 experiments obtained from cells isolated from livers of 3 WT and 3 CB1 −/− mice and are expressed as percent of control. (p is inferior to 0.05). Error bars are shown on the plot.

Figure 4:
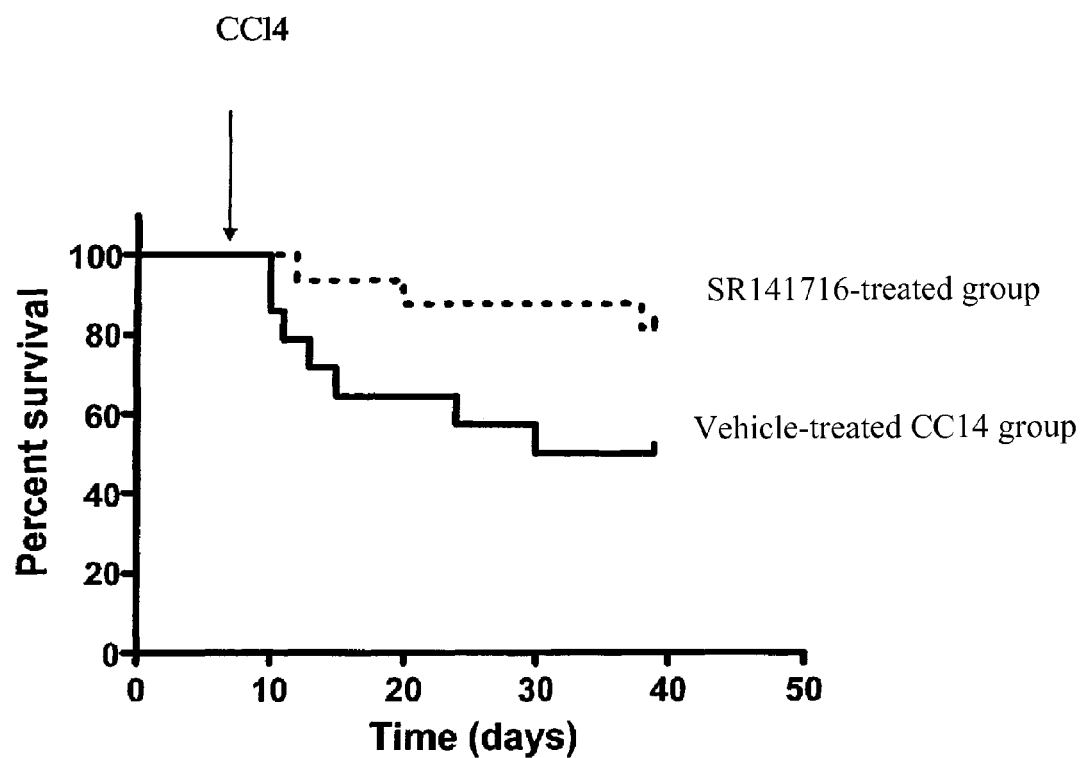

FIG. 4: Plot showing the effect of SR141716 or its vehicle on the mortality induced by carbon tetrachloride in mice. The survival rate of mice treated with CCl$_4$ either with SR141716 (dotted lines) or with no treatment (solid lines showing the administration of vehicle only without CB1 antagonist) is shown against time in days. Time of administration of CCl4 is shown by the arrow.

DETAILED DESCRIPTION OF EMBODIMENTS OF THE INVENTION

The present invention provides for methods and compositions (such as pharmaceutical compositions) for treating hepatic diseases which includes liver fibrosis. The hepatic diseases also include, but are not limited to, alcoholic liver cirrhosis, chronic viral hepatitis, non alcoholic steatohepatitis and primary liver cancer.

The applicant has shown that the downregulation of CB1 receptors and the use of antagonist or reverse agonist to the CB1 receptor constitutes a treatment for various types of liver fibrosis. This is shown by several experiments.

Firstly, the role of CB1 receptors in the progression of liver fibrosis was studied in CB1 receptor knock-out mice engineered to lack expression of CB1 receptors (CB1 KO, n=15) and their wild type counterpart (WT, n=12) in a model of chronic carbon tetrachloride intoxication inducing fibrosis. Fibrosis and necroinflammation were assessed by a METAVIR-derived score. CB1KO mice showed reduced fibrosis compared to WT animals (fibrosis score: 2.59±0.13 vs 3.33±0.13, p<0.05). Accordingly, hepatic collagen, assessed by hydroxyproline determination was decreased by 40% in CB1KO mice, as compared with WT animals (0.46±0.06 vs 0.73±0.11 mg/mg tissue, p<0.05). The necroinflammatory score was similar in both groups. Such inactivation of CB1 receptor is phenotypically equivalent to a perfect antagonistic block of the CB1 receptor by pharmaceutical means. Liver fibrosis is strongly reduced in CB1 knockout mice as compared to control mice, based on both histological analysis of the livers and measurement of hydroxyproline content, a specific biochemical marker of collagen deposition. In addition, it was shown that the expression of TGF-β1 and smooth muscle a actin were reduced in CB1 deficient mice compared with wild type mice when treated with CCl4. Finally it was shown that CB1 inactivation increases apoptosis in murine hepatic myofibroblasts. Therefore, the inactivation of CB1 receptor reduces hepatic fibrosis.

Secondly, immunohistochemical labelling was performed with human normal, cirrhotic liver and cultured hepatic myofibroblasts. Immunochemistry showed a faint expression of CB1 receptors in normal liver (n=3), contrasting with a marked upregulation in cirrhotic samples of various etiologies (n=13), predominating in nonparenchymal cells within and at the edge of fibrous septa. Double immunohistochemistry identified myofibroblasts as a main source of CB1 receptors, and accordingly, CB1 receptors were also expressed in cultured human hepatic myofibroblasts. CB1 receptors are faintly expressed by intrasinusoidal cells in the normal liver and are markedly upregulated during chronic liver diseases. Double immunohistochemistry revealed hepatic myofibroblasts as a prominent cell type expressing CB1 receptors in the cirrhotic liver. Therefore, CB1 receptor expression and activity correlate with hepatic fibrosis.

Thirdly, epidemiological studies were performed in a cohort of patients with chronic hepatitis C and showed that daily *cannabis* smoking is a risk factor for fibrosis progression in chronic hepatitis C as the rate of fibrosis is greater in these patients compared with non *cannabis* smokers. This demonstrates a participation of cannabinoid signal transduction in the fibrosis of the liver. Therefore the cannabinoid signalling pathway is involved in hepatic fibrosis.

Fourthly, in vitro studies of the effects of the CB1 receptor antagonist N-piperidino-5-(4-chlorophenyl)-1-(2,4-dichlorophenyl)-4-methylpyrazole-3-carboxamide known commercially as SR141716 (or SR141716A) or rimonabant, were performed on hepatic myofibroblast cultures from both humans and mice showing that a CB1 antagonist can inhibit hepatic myofibroblast growth. This compound and its preparation are described in the European patent application EP656354-A1 and is represented by formula I:

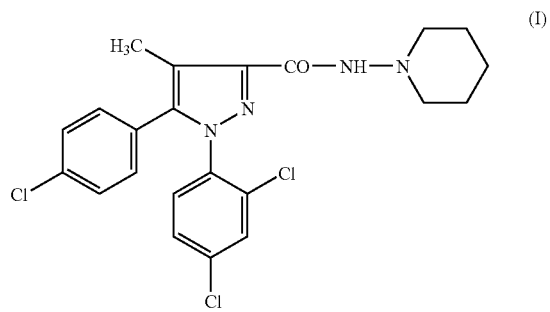

Such an antagonist to CB1 and the pharmaceutically acceptable salts thereof can be prepared according to European patent application EP656354, and similarly the pharmaceutical compositions can be prepared according to the description of that same patent.

Fifthly, in vivo studies on mice showed that the CB1 antagonist SR141716 could reduce the lethality induced by carbon tetrachloride which is a model of induced liver fibrosis.

Antagonists to the CB1 receptor are herein defined as compounds able to inhibit the activation or the expression of CB1 receptor.

Compounds capable of inhibiting the activation of CB1 receptor include in particular those able to interact with agonists of CB1 receptors, to inhibit the binding of said agonists, or to inhibit the activation of CB1 receptor resulting from said binding.

In particular, suitable antagonists to the CB1 receptor can be specific to CB1 or not, and include reverse agonists. These antagonists also include the substituted amides described in WO 03/077847, the substituted aryl amides described in WO 03/087037, the substituted imidazoles described in WO 03/063781, bicyclic amides described in WO 03/086288, the terphenyl derivatives described in WO 03/084943, the N-piperidono-3-pyrazolecarboxamide and N-piperidino-5-(4-chlorophenyl)-1-(2,4-dichlorophenyl)-4-methylpyrazole-3-carboxamide described in EP-B-656354, the aryl-benzo[b]thiophene and benzo[b]furan compounds respectively described in U.S. Pat. Nos. 5,596,106 and 5,747,524, the azetidine derivatives described in FR2805817, 3-amino-azetidine described in FR2805810, or the 3-Substituted or 3,3-disubstituted 1-(di-((hetero)aryl)-methyl)-azetidine derivatives described in FR2805818, N-(piperidin-1-yl)-1-(2,4-dichlorophenyl)-5-(4-iodophenyl)-4-methyl-1H-pyrazole-3-carboxamide (known as AM251) and the compound commercially known as LY-320135. Suitable CB1 antagonists also include N-piperidino-5-(4-bromophenyl)-1-(2,4-dichlorophenyl)-4-ethylpyrazole-3-carboxamide described in patent EP 1150961.

Other suitable CB1 antagonists are described in patent EP576357 and include a compound of the formula II in which $g_2$, $g_3$, $g_4$, $g_5$ and $g_6$ and $w_2$, $w_3$, $w_4$, $w_5$ and $w_6$ are identical or different and are independently hydrogen, a chlorine or bromine atom, a ($C_1$-$C_3$) alkyl, a ($C_1$-$C_3$) alkoxy, a trifluoromethyl or a nitro group and $g_4$ is optionally a phenyl group; $R_4$ is hydrogen or a ($C_1$-$C_3$) alkyl; X is either a direct bond or a group —$(CH_2)_x$—$N(R_3)$—, in which $R_3$ is hydrogen or a ($C_1$-$C_3$) alkyl and x is zero or one; R is: a group —$NR_1R_2$ in which $R_1$ and $R_2$ are independently a ($C_1$-$C_6$)-alkyl; an non-aromatic ($C_3$-$C_{15}$) carbocyclic radical which is optionally substituted, said substituent(s) being other than a substituted carbonyl; an amino ($C_1$-$C_4$) alkyl group in which the amino is optionally disubstituted by a ($C_1$-$C_3$) alkyl; a cycloalkyl ($C_1$-$C_3$) alkyl in which the cycloalkyl is $C_3$-$C_{12}$; a phenyl which is unsubstituted or monosubstituted or polysubstituted by a halogen, by a ($C_1$-$C_5$) alkyl or by a ($C_1$-$C_5$) alkoxy; a phenyl ($C_1$-$C_3$) alkyl; a diphenyl ($C_1$-$C_3$) alkyl; a naphthyl; an anthracenyl; a saturated 5- to 8-membered heterocyclic radical which is unsubstituted or substituted by a ($C_1$-$C_3$) alkyl, by a hydroxyl or by a benzyl; a 1-adamantylmethyl; an aromatic heterocycle which is unsubstituted or monosubstituted or polysubstituted by a halogen, by a ($C_1$-$C_5$) alkyl or by a ($C_1$-$C_5$) alkoxy; a ($C_1$-$C_3$) alkyl which is substituted by an aromatic heterocycle which is unsubstituted or monosubstituted or polysubstituted by a halogen, by a ($C_1$-$C_5$) alkyl or by a ($C_1$-$C_5$) alkoxy; or else $R_1$ is hydrogen and $R_2$ is as defined above; or else $R_1$ and $R_2$ form a saturated 5- to 8-membered heterocyclic radical with the nitrogen atom to which they are bonded, said heterocyclic radical being other than morpholine when $w_2$, $w_3$, $w_4$, $w_5$, $w_6$, $g_2$, $g_3$, $g_4$, $g_5$ and $g_6$ are all hydrogen; a group $R_2$ as defined above when X is —$(CH_2)_xN(R_3)$—; a group $R_5$ when X is a direct bond, $R_5$ being a ($C_1$-$C_3$) alkyl; a ($C_3$-$C_{12}$) cycloalkyl which is unsubstituted or substituted by a ($C_1$-$C_5$) alkyl; a phenyl ($C_1$-$C_3$) alkyl which is unsubstituted or substituted by a halogen or by a ($C_1$-$C_5$) alkyl; a cycloalkyl ($C_1$-$C_3$) alkyl in which the cycloalkyl is $C_3$-$C_{12}$ and is unsubstituted or substituted by a ($C_1$-$C_5$) alkyl; or a 2-norbornylmethyl;

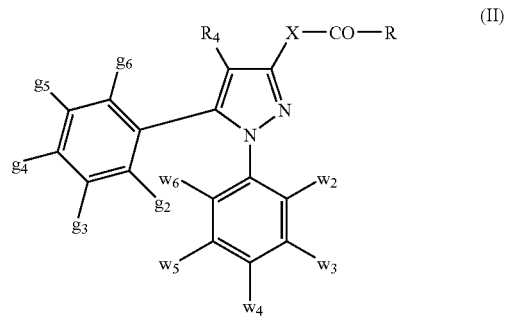

(II)

These results are not confined to humans and can be applied to mammals in general.

The compositions containing the CB1 antagonist(s) can be administered for prophylactic and/or therapeutic treatments. The active ingredient (e.g., CB1 receptor antagonist(s)) in the pharmaceutical composition is present in an "effective amount." By an "effective amount" of a pharmaceutical composition is meant a sufficient, but non-toxic amount of the agent to provide the desired effect. The term refers to an amount sufficient to treat a subject (e.g., a mammal, particularly a human). Thus, the term "therapeutic amount" refers to an amount sufficient to remedy a disease state or symptoms, by preventing, hindering, retarding or reversing the progression of the disease or any other undesirable symptoms whatsoever. The term "prophylactically effective" amount refers to an amount given to a subject that does not yet have the disease, and thus is an amount effective to prevent, hinder or delay the onset of a disease.

In therapeutic applications, compositions are administered to a patient already suffering from a disease, as described, in an amount sufficient to cure or at least partially stop the symptoms of the disease and its complications. An appropriate dosage of the pharmaceutical composition is readily determined according to any one of several well-established protocols. For example, animal studies (for example on mice or rats) are commonly used to determine the maximal tolerable dose of the bioactive agent per kilogram of weight. In general, at least one of the animal species tested is mammalian. The results from the animal studies can be extrapolated to determine doses for use in other species, such as humans for example. What constitutes an effective dose also depends on the nature and severity of the disease or condition, and on the general state of the patient's health.

In prophylactic applications, compositions containing, for example CB1 receptor antagonists, are administered to a patient susceptible to or otherwise at risk of a hepatic disease. Such an amount is defined to be a "prophylactically effective" amount or dose. In this use, the precise amount depends on the patient's state of health and weight.

In both therapeutic and prophylactic treatments, the antagonist contained in the pharmaceutical composition can be administered in several dosages or as a single dose until a desired response has been achieved. The treatment is typically monitored and repeated dosages can be administered as necessary. Compounds of the invention may be administered according to dosage regimens established whenever inactivation of CB1 receptors is required.

The daily dosage of the products may be varied over a wide range from 0.01 to 1,000 mg per adult per day. Preferably, the compositions contain 0.01, 0.05, 0.1, 0.5, 1.0, 2.5, 5.0, 10.0, 15.0, 25.0, 50.0, 100, 250 and 500 mg of the active ingredient for the symptomatic adjustment of the dosage to the patient to be treated. A medicament typically contains from about 0.01 mg to about 500 mg of the active ingredient, preferably from 1 mg to about 100 mg of the active ingredient. An effective amount of the drug is ordinarily supplied at a dosage level from 0.0002 mg/kg to about 20 mg/kg of body weight per day, especially from about 0.001 mg/kg to 10 mg/kg of body weight per day. It will be understood, however, that the specific dose level and frequency of dosage for any particular patient may be varied and will depend upon a variety of factors including the activity of the specific compound employed, the metabolic stability, and length of action of that compound, the age, the body weight, general health, sex, diet, mode and time of administration, rate of excretion, drug combination, the severity of the particular condition, and the host undergoing therapy.

In the pharmaceutical compositions of the present invention for oral, sublingual, subcutaneous, intramuscular, intravenous, transdermal, local or rectal administration, the active principle, alone or in combination with another active principle, can be administered in a unit administration form, as a mixture with conventional pharmaceutical supports, to animals and human beings. Suitable unit administration forms comprise oral-route forms such as tablets, gel capsules, powders, granules and oral suspensions or solutions, sublingual and buccal administration forms, aerosols, implants, subcutaneous, transdermal, topical, intraperitoneal, intramuscular, intravenous, subdermal, transdermal, intrathecal and intranasal administration forms and rectal administration forms.

The appropriate unit forms of administration include forms for oral administration, such as tablets, gelatine capsules, powders, granules and solutions or suspensions to be taken orally, forms for sublingual and buccal administration, aerosols, implants, forms for subcutaneous, intramuscular, intravenous, intranasal or intraocular administration and forms for rectal administration.

In the pharmaceutical compositions of the present invention, the active principle is generally formulated as dosage units containing from 0.5 to 1000 mg, preferably from 1 to 500 mg, more preferably from 2 to 200 mg of said active principle per dosage unit for daily administrations.

When preparing a solid composition in the form of tablets, a wetting agent such as sodium laurylsulfate can be added to the active principle optionally micronized, which is then mixed with a pharmaceutical vehicle such as silica, gelatine, starch, lactose, magnesium stearate, talc, gum arabic or the like. The tablets can be coated with sucrose, with various polymers or other appropriate substances or else they can be treated so as to have a prolonged or delayed activity and so as to release a predetermined amount of active principle continuously.

A preparation in the form of gelatin capsules is obtained by mixing the active principle with a diluent such as a glycol or a glycerol ester and pouring the mixture obtained into soft or hard gelatine capsules.

A preparation in the form of a syrup or elixir can contain the active principle together with a sweetener, which is preferably calorie-free, methyl-paraben and propylparaben as an antiseptic, a flavoring and an appropriate color.

The water-dispersible powders or granules can contain the active principle mixed with dispersants or wetting agents, or suspending agents such as polyvinyl-pyrrolidone, and also with sweeteners or taste correctors.

Rectal administration is effected using suppositories prepared with binders which melt at the rectal temperature, for example cacao butter or polyethylene glycols.

Parenteral, intranasal or intraocular administration is effected using aqueous suspensions, isotonic saline solutions or sterile and injectable solutions which contain pharmacologically compatible dispersants and/or wetting agents, for example propylene glycol, butylene glycol, or polyethylene glycol.

Thus a cosolvent, for example an alcohol such as ethanol or a glycol such as polyethylene glycol or propylene glycol, and a hydrophilic surfactant such as Tween® 80, can be used to prepare an aqueous solution injectable by intravenous route. The active principle can be solubilized by a triglyceride or a glycerol ester to prepare an oily solution injectable by intramuscular route.

Transdermal administration is effected using multilaminated patches or reservoirs into which the active principle is in the form of an alcoholic solution.

Administration by inhalation is effected using an aerosol containing for example sorbitan trioleate or oleic acid together with trichlorofluoromethane, dichlorotetrafluoroethane or any other biologically compatible propellant gas.

The active principle can also be formulated as microcapsules or microspheres, optionally with one or more carriers or additives.

Among the prolonged-release forms which are useful in the case of chronic treatments, implants can be used. These can be prepared in the form of an oily suspension or in the form of a suspension of microspheres in an isotonic medium.

The active principle can also be presented in the form of a complex with a cyclodextrin, for example alpha.-, beta.- or .gamma.-cyclodextrin, 2-hydroxypropyl-.beta.-cyclodextrin or methyl-.beta.-cyclodextrin.

Another suitable antagonist of CB1 receptor can consist in an antibody directed to CB1 receptor which impedes the binding of the agonists to CB1 receptor.

There exists various isoforms of the CB1 receptors and other variants. Accordingly the use of antagonists to any of these variant CB1 receptors would not take one outside of the field of the invention. Generally and in addition to protein sequence identity or homology, the biological function of a CB1 receptor can be defined by being a G protein-coupled cellular receptor, capable of binding THC and transducing a cellular signal. The skilled worker would be able to test the CB1 receptor function by known standard procedures. These could include the expression of putative CB1 cDNA in CHO cells, the subsequent testing using CB1 ligands and the measurement of the cell signalling activity of the activated putative CB1 receptor, for example by the measurement of cyclic AMP production.

An alternative to reducing the signal transduction of cannabinoids through the CB1 receptor by pharmacological means, involves the downregulation or suppression of that receptor. There exist various known techniques for downregulating or suppressing the expression of genes that the skilled worker will be able to use. A non-exhaustive list involves inactivation by homologous recombination (Gossen, J, trends Genet. 9:27-31, 1993), RNA interference (Elbashir S. M., Nature. 2001 May 24; 411(6836):428-9), the expression of dominant negative receptors (Dosil, M. et al, Mol Cell Biol. 1998 October, 18(10):5981-91) and the transgenic expression of suppressing transcription factors.

It is also possible to screen for CB1 antagonists with selective anti-fibrotic properties by using myofibroblast cultures obtained by outgrowth of explants prepared from surgical specimens of normal human liver, as previously described (Li, L. et al, *Gastroenterology* 125, 460-9 (2003), Davaille J et al., *J Biol Chem* (2002)). In particular, a method of screening for CB1 antagonists with selective anti-fibrotic properties involves the steps of:

a) preparing multiple cell cultures of myofibroblasts,
b) exposing each of the cell cultures to one of the compounds to be tested,
c) assessing the effects of the compounds on the fibrogenic properties of the myofibroblasts, by evaluating their effects on the survival and growth of these cells,
d) selecting one the compounds tested.

An alternative method would be as above, wherein step c) involves assessing the effects of the compounds on the fibrogenic properties of the myofibroblasts, by evaluating their effects on their capacity to synthesize extracellular matrix and components that inhibit its degradation.

An alternative method would be as above wherein step c) involves assessing the effects of the compounds on the fibrogenic properties of the myofibroblasts, by evaluating cytokine production and migration.

The skilled worker would be able to perform these individual steps using well known procedures, such as described in Li, L. et al, *Gastroenterology* 125, 460-9 (2003), Davaille J et al., *J Biol Chem* (2002), Li L et al., *J Biol Chem* 2001 et Davaille, J. et al., *J Biol Chem* 275, 34628-33 (2000).

The compounds isolated by such means can then be used for the manufacture of a composition for the treatment of hepatic diseases.

EXAMPLES

Example 1

CB1 Receptors Upregulation in Human Cirrhotic Liver

Materials.

Culture media and reagents were from Gibco (Invitrogen, France). Fetal calf serum was from JBio Laboratories (France). Pooled human AB positive serum was supplied by the National Transfusion Center. The rabbit anti-CB1 receptor antiserum (raised against residues 1-14 of the human CB1 receptor) and CB1 blocking peptide (residues 1-14 of the human CB1 receptor) were from Cayman (Spibio, France).

RNA Preparation and RT-PCR.

Total RNA was extracted from confluent quiescent cells in 100 mm dishes, using Rneasy kit (Qiagen, France). CDNA was synthesized from 2 µg of total RNA by reverse transcription fro 1 h at 37° C., using 200 units of M-MLV reverse transcriptase (Invitrogen, France), in a 20 µl reaction mixture containing 0.05 µg/µl oligo $(dT)_{12-18}$ primers (Invitrogen, France), 0.5 mM dNTPs (Promega, France) and 10 mM dithiothreitol in first strand buffer (Invitrogen, France). To check for eventual genomic DNA contamination, controls were performed in the same conditions without reverse transcriptase. PCRs were performed with 2 µl of the reverse transcription reaction, using 1.25 units of AmpliTaq Gold DNA polymerase (Applied Biosystems, France) and the corresponding buffer supplemented with 2 mM $MgCl_2$, 0.2 mM dNTPs, and 25 pmol of each primer in a total volume of 50 µl. 40 PCR cycles were carried out in a GeneAmp 2700 thermal-cycler (Applied Biosystems, France), each cycle consisting of denaturation at 95° C. for 45 s, annealing at 58° C. for 45 s, and extension at 72° C. for 30 s, with the first cycle containing an extended denaturation period (10 min) for the activation of the polymerase and the last cycle containing an extended elongation period (10 min). Oligonucleotide primers (MWG Biotech, France) for CB1 were as follows: CB1 sense primer 5 '-TTTGGCTACACACAATTGGAAGTCTAA-GAACCCC-3' (SEQ ID NO:10) and CB1 antisense primer, 5'-GCACACATTGACACGTATCCACTGCTTG-3' (SEQ ID NO:11), with a predicted PCR product of 287 bp. PCR amplified products were analyzed on a 1.5% agarose gel, and blotted onto Hybond-N+membrane (Amersham Pharmacia Biotech, France). After a prehybridization in a buffer containing 6XSSC, 5 mM EDTA pH 8, 5×denhardt, 0.1% SDS and 0.1 mg/mi ssDNA, for 2 h at 42° C., the membrane was hybridized overnight at 42° C. in the same buffer containing 50 ng of the CB1 oligonucleotide probe 5'-CCTGTGAGAT-GTGTATCAGTGTTTATGTGC-3' (SEQ ID NO:13), labeled with [$\gamma$-$^{32}$P] adenosine triphosphate, using T4 kinase (Invitrogen, France). After hybridization, the blot was washed twice in 0.1% SDS, 1XSSC for 30 min at room temperature and analyzed by phospho-imager (Molecular Dynamics, France).

Human Liver Specimen.

Snap frozen surgical liver resections from 13 patients (8 men, 5 women, mean age 55 years, 39-72 range years) were retrospectively studied. Normal liver samples were collected from 3 women undergoing hepatic resection for colorectal metastasis (n=3). Cirrhotic samples were obtained from 8 livers of patients undergoing liver transplantation and from 2 patients undergoing hepatic resection for hepatocellular carcinoma. Cirrhosis was consecutive to chronic HCV (n=1) or HBV (n=2) infections, primary biliary cirrhosis (n=1), alcoholic liver disease (n=4), or Wilson disease (n=1) and remained cryptogenic in 1 case.

Immunohistochemical Detection of CB1 Receptors in Normal and Cirrhotic Livers.

Frozen sections (5-7 µm) were air-dried and fixed in ice-cold acetone for 10 minutes at −20° C. Non specific binding was blocked by preincubating sections 1 h at room temperature with 20% human serum in 50 mM Tris-buffered saline (TBS) pH 7.6. Sections were further incubated overnight at 4° C. with a rabbit polyclonal antiserum to human CB1 receptor (Cayman, Spibio, France), diluted 1/2000 in antibody diluent (Dakopatts, France). After rinsing 3 times in TBS, sections were incubated for 45 min at room temperature with mouse monoclonal anti-rabbit immunoglobulin G antibodies (Dakopatts, France), diluted 1/50, rinsed 3 times in TBS, further incubated for 30 min at room temperature with rabbit anti-mouse immunoglobulin antibodies (Dakopatts, France), diluted 1/50, and then processed using the alkaline phosphatase-anti-alkaline phosphatase (APAAP) complex immunoenzymatic method, as described in the publication Li, L. et al, *Gastroenterology* 125, 460-9 (2003). To confirm the specificity of the primary antibody, controls included preadsorption of the primary antibody with the corresponding synthetic peptide (100 µg/ml, for 1 h at room temperature) or omission of the primary antibody. In order to determine whether hepatic myofibroblasts express CB1 protein, double immunostaining of CB1 and smooth muscle α-actin was performed. Sections were first processed for CB1 immunostaining using a standard three-stage biotin-streptavidin immunoperoxidase method. Briefly endogenous peroxidase was quenched by incubation of the acetone fixed sections in TBS/0.3% $H_2O_2$ for 30 min, then washed in TBS. Non specific binding was blocked by preincubating sections 30 min with TBS/20% human serum. Sections were then incubated for 15 min in avidin followed by 15 min in biotin (Vector Laboratories, Avidin/Biotin blocking kit), and further incubated over night at 4° C. with the anti-CB1 antiserum. Subsequently, sections were washed in TBS and incubated successively with the secondary antibody biotinylated goat anti-rabbit (Dakopatts, France) (1/500) and streptavidin-horseradish peroxidase complex (1/50) (Pierce, Perbio, Interchim, France), 30 min each. Peroxidase activity was revealed using metal-enhanced diaminobenzidine (DAB) substrate (Pierce, Interchim, France). All steps were carried out at room temperature unless otherwise mentioned. Immunostaining for smooth muscle α-actin was then processed using the APAAP method described above, with a 1/5000 dilution of a monoclonal antibody to smooth muscle α-actin (Sigma, France). Slides were counterstained with aqueous haematoxylin. Single and double staining were visualized by bright-field photomicrographs on an Axioplan microscope (Zeiss, Oberkochen, Germany), equipped with a digital imaging system (Hamamatsu 3CCD color camera, Hamamatsu Photonics, France).

Isolation and Culture of Human Hepatic Myofibroblasts.

Human hepatic myofibroblasts were obtained by outgrowth of explants prepared from surgical specimens of normal liver obtained from surgery of benign or malignant liver tumors, as described in Davaille, J. et al., *J Biol Chem* 275, 34628-33 (2000). Cells were cultured in Dulbecco's modified Eagle's medium (DMEM) containing 10% serum (5% fetal calf serum, and 5% human serum, DMEM 5/5) and were used between the third and seventh passage. Experiments were performed on cells that were made quiescent by a 48 h incubation in serum-free Waymouth medium unless otherwise indicated. The myofibroblastic nature of these cells was evaluated as described in Davaille, J. et al., *J Biol Chem* 275, 34628-33 (2000), and they display the phenotypic and functional characteristics of the fibrogenic cells found in situ during hepatic fibrogenesis (Win, K. M. et al., *Hepatology* 18, 137-45 (1993). The cultures were found to express smooth muscle α-actin and two markers of hepatic myofibroblasts, fibulin-2 and interleukin-6 (Davaille, J. et al., *J Biol Chem* 275, 34628-33 (2000)).

Immunocytochemical Detection of CB1 Receptors in Cultured Human Hepatic Myofibroblasts.

Human hepatic myofibroblasts were seeded (10,000/cm$^2$) in 35 mm dishes, grown in serum-containing medium for 24 h, serum-deprived for 48 h, washed with TBS and fixed in 4% paraformaldehyde for 10 min. After washing once in TBS, cells were incubated in TBS containing 20% human serum for 30 min at room temperature, and further incubated with the anti-CB1 antiserum (1/500 dilution in TBS/20% human serum) for 3 h at room temperature and overnight at 4° C. in a humid chamber. Cells were then rinsed extensively in TBS, incubated with a Cy3-conjugated goat anti-rabbit IgG (Sigma, France) (1/50 dilution in TBS/20% human serum) at room temperature, in the dark, for 30 min, washed, covered with VECTASHIELD Mounting Medium (Vector Laboratories, Burlingame, Calif.), and viewed under fluorescence miscroscopy. To confirm the specificity of the primary antibody, controls included preadsorption with the corresponding synthetic peptide (100 µg/ml, for 1 h at room temperature) or omission of the primary antibody.

CB1 receptor expression was studied by immunohistochemistry with a polyclonal antibody directed against the human CB1 receptor, on frozen tissue sections prepared from surgical samples of normal (n=3) and cirrhotic livers (n=10), with various etiologies (chronic HCV n=1 or HBV n=2, primary biliary cirrhosis n=1, alcoholic liver disease n=4 or Wilson disease n=1 and remained cryptogenic in one case). In normal liver, a discrete, punctuate, CB1 immunoreactivity was detected along sinusoidal walls. In the cirrhotic liver, the overall intensity of the CB1 immunostaining markedly increased, irrespective of the etiology of cirrhosis. CB1 was mostly evident in numerous spindle-shaped cells distributed along the fibrotic septa. CB1 receptor expression was also found in other non parenchymal cells, including inflammatory cells and ductular proliferating cells located along the fibrotic septa. Specificity of the antibody was demonstrated by the lack of signal in sections incubated in the presence of the CB1 blocking peptide or in the absence of the first antibody.

Double immunohistochemistry, using an anti-CB1 receptor antibody and an anti-smooth muscle α-actin antibody, clearly identified hepatic myofibroblasts within fibrotic septa as a prominent cell type expressing CB1 receptors. Accordingly, CB1 receptors were also expressed in cultured human hepatic myofibroblasts, as demonstrated by both RT-PCR analysis and immunocytochemistry.

Example 2

Reduced Fibrogenic Response in CB1 Deficient Mice

Animals and Experimental Design.

Male CD1 mice invalidated for CB1 receptors and wild type littermates were generated as previously described in the publication Ledent, C. et al., *Science* 283, 401-4. (1999). Heterozygous mice were bred for more than fifteen generations on a CD1 background, before generating the wild type and mutant mice used in the present study. Forty male: WT (n=20) and CB1−/− (n=20), aged 8-10 weeks, were used and animals were divided into the following groups: WT sham (olive oil n=8); WT CCl4 (n=12); CB1−/− sham (olive oil n=5); CB1−/− CCl4 (n=15). Animals were housed in temperature and humidity controlled rooms, kept on a 12-h light/dark cycle and provided unrestricted amounts of food and water, unless otherwise specified. Fibrosis was induced by giving carbon tetrachloride (CCl4) (Sigma, St Quentin-Fallavier, France) mixed with olive oil (1 vol:10 vol) at 0.5 ml/kg body weight, by intra peritoneal injection (IP), twice a week, in alternate with an equal volume of ethanol mixed with Cremophor and PBS (May 5, 1990) three times a week. Sham animals for CCl4 received olive oil. After 4 weeks, the animals were starved overnight and killed 48 h after the last CCl4 injection. Liver samples were taken from several lobes and either i) snap-frozen in liquid nitrogen and homogenized in RNA extraction solution, ii) homogenized in H$_2$O and snap frozen in liquid nitrogen for hydroxyproline determination or iii) fixed in buffered formalin. Snap frozen sample were stored at −80° C. until use. Blood samples were also collected in siliconed tubes containing inert gel barrier and clot activator disc (Venoject, Terumo, France), serum separated by centrifugation and stored at −20° C. until use.

Liver-Function Tests.

Routine liver-function blood tests (bilirubin, alkaline phosphatase, and aspartate transaminase) were performed on an automated analyzer.

Fibrosis, Inflammation and Necrosis Assessment.

Liver specimen were fixed in 10% formalin and paraffin-embedded. Tissue sections (4 µm-thick) were stained with hematoxylin-eosin (H&E) for routine examination, or with Picro-Sirius red for vizualization of hepatic collagen deposition. Histological grading (necrosis and inflammatory infiltration) and staging (fibrosis) were blindly assessed on at least 4 fragments from different areas of each liver, by an independent anatomopathologist. Fibrosis was staged on a scale of 0 to 4, according to a semi-quantitative modified METAVIR scoring system, as follows: no fibrosis=0, portal fibrosis without septa=1, few septa=2, numerous septa without cirrhosis=3, and cirrhosis=4. Heterogeneity of fibrosis throughout the liver, when present, was taken into account by estimating the percent area corresponding to an individual score level in every fragment and by combining data for each liver. Necrosis, defined by acidophilic bodies, ballooning degeneration and/or scattered foci of hepatocellular necrosis, was graded as follows: absent=0, mild=1 (involvement of ⅓ of lobules or nodules), moderate (involvement of ⅓-⅔ of lobules or nodules)=2, marked (involvement more than ⅔ of lobules or nodules)=3. Inflammatory infiltration was graded from 0 to 3: none=0, mild (portal and/or lobular) inflammatory infiltration in less than ⅓ of lobules or nodules=1, moderate (portal and/or lobular) inflammatory infiltration involving ⅓-⅔ of lobules or nodules=2, marked (portal and/or lobular) inflammatory infiltration involving more than 2/3 of lobules or nodules=3. All samples were scored simultaneously.

Hydroxyproline Content.

Hydroxyproline content was assessed as previously described in the publication Grenard, P et al., *J Hepatol* 26, 1356-62. (1997). Three small fragments of each liver were pooled, homogenized in distilled water, lyophilized and overnight hydrolyzed in 6 N HCl at 110° C. (10 mg of dry liver powder/ml HCl 6N). The hydrolyzates were then treated with activated charcoal, filtered, evaporated and resuspended in distilled water. Aliquots of the hydrolyzates were used to measure hydroxyproline (HP) content spectrophotometrically by reacting with Ehrlich's reagent according to the method of Woessner (Woessner, J. F., *Arch Biochem Biophys* 93, 440-7 (1961)) modified as described in the publication Creemers, L. B et al., Biotechniques 22, 656-8 (1997). The hepatic hydroxyproline content is expressed as micrograms per milligram of tissue (dry weight).

Isolation and Culture of Mice Hepatic Myofibroblasts.

Mice myofibroblasts were isolated by collagenase perfusion and purified by density gradient in Nicodenz, as described in Vrochides, D., et al Hepatology, 1996. 23(6): p. 1650-5. After isolation, cells were cultured in DMEM medium containing 20% fetal calf serum. At day one, cell debris and non-adherent cells were removed by washing, and the cells were further cultured in DMEM medium containing 10% FCS. Cells were used between the third and ninth passage, and were found to express smooth muscle alpha-actin, fibulin-2 and interleukin-6.

Measurement of Caspase-3 Like Activity.

Apoptosis assays were performed on non-confluent cells allowed to attach overnight in DMEM containing 10% FCS and serum-starved during the indicated time. Caspase-3-like activity was assayed on cell lysates using AC-DEVD-AFC as substrate, as previously described (Davaille, J., et al., J Biol Chem, 2002. 277(40): p. 37323-30; Li, L., et al, J Biol Chem, 2001. 276(41): p. 38152-8).

Assessment of Cell Viability.

Mice hepatic myofibroblasts (7,000 cells/well in 96-well plates) were allowed to attach overnight in DMEM 10%, serum-starved during the indicated time. CellTiter 96 AQueous One Solution reagent was added to each well and absorbance was recorded at 490 nm.

Determination of Hepatic TGF-β1.

Hepatic TGF-β1 content was determined in acid-activated whole-liver homogenates. Frozen liver samples were homogenized in lysis buffer (25 mM HEPES pH 7.4, 1% NP40, 5 mM MgCl2, 1.3 mM EDTA, 1 mM EGTA, phosphatase and protease inhibitors) for 30 min at 4° C. After centrifugation at 12,000 g for 10 min at 4° C., cleared tissue lysates were collected and stored at −80° C. until analysis. Protein concentration was determined by BCA Protein Assay (Pierce) using bovine serum albumin (BSA) as a standard. To activate latent TGF-β1 to immunoreactive form, tissue lysates were acidified in an equal volume of 2.5 N acetic acid, 10M urea at room temperature for 10 min, followed by a neutralisation using 2.7 M NaOH in 1M HEPES. ELISA was performed using murine TGF-β1 Quantikine (R&D Systems, France) following the manufacturer's instructions. Murine TGF-β1 recombinant protein was used as a standard. The results are expressed as pg of TGF-β1/mg soluble protein.

Immunohistochemical Staining for Smooth Muscle α-Actin.

Liver tissue was fixed in formalin and embedded in paraffin. Immunohistochemical staining for smooth muscle α-actin was performed using the Vector M.O.M. immunodetection kit, and according to the protocol specified by the manufacturer (Vector Laboratories). Briefly, paraffin-embedded sections were deparaffinized and rehydrated through xylene and ethanol into TBS (50 mM Tris, 150 mM NaCl, pH 7.6). Slides were microwaved in citrate buffer at a power of 700 W for 2 times for 5 minutes each. Endogenous peroxidase activity was then quenched by incubation for 1 hour in 0.3% H2O2 in TBS. After blocking nonspecific binding was by preincubating sections with 1.5% horse serum in TBS for 1 hour, sections were incubated for 15 min in avidin, followed by 15 min in biotin (Avidin/Biotin blocking kit, Vector Laboratories), and further incubated with the MOM Mouse Ig Blocking solution for 1 hr. Sections were subsequently washed in TBS, and successively incubated with the MOM diluent solution for 5 min, with a 1:1000 dilution of a monoclonal antibody to smooth muscle α-actin for 30 min (Sigma, France), with the MOM Biotinylated anti-mouse IgG Reagent for 10 min and finally with the Vectastain ABC Reagent for 5 min. Peroxidase activity was revealed using metal-enhanced diaminobenzidine (DAB) substrate (Pierce, Interchim, France). All steps were carried out at room temperature. Control slides stained with the MOM diluent instead of the primary antibody did not show any positive staining. The area of positive staining was measured on 4-5 liver fragments per animal, using a morphometric analysis system with Image-Pro Plus software (MediaCybernetics, MicroMecanique, France).

Statistics.

Results are expressed as mean ±SEM of n experiments. Results were analyzed by two-way analysis of variance (ANOVA) followed by paired comparisons corrected according to the Student-Newmann-Keuls method. $p < 0.05$ was taken as the minimum level of significance.

CB1 receptor-deficient mice (CB1−/−) and their wild type littermates (WT) were exposed to chronic CCl4 treatment. Sham mice (CB1−/− and WT) received olive oil. The mean body weight, liver weight and liver weight/body weight ratio did not significantly differ between the four experimental groups as shown in Table 1.

TABLE 1

Vital Parameters and Liver-Function Tests in mice wild type (WT) or CB1 deficient after 4 Weeks of CCl4 Treatment

| Parameter | WT Olive oil | WT CCl4 | CB1−/− Olive oil | CB1−/− CCl4 |
| --- | --- | --- | --- | --- |
| Body weight (g) | 36.3 ± 1.7 | 35.2 ± 0.8 | 34.8 ± 2.1 | 36.6 ± 0.9 |
| Liver weight (g) | 1.9 ± 0.1 | 2.1 ± 0.1 | 1.8 ± 0.1 | 2.1 ± 0.1 |
| Liver weight/ Body weight ratio(×100) | 5.26 ± 0.45 | 6.0 ± 0.3 | 5.4 ± 0.4 | 5.7 ± 0.1 |

TABLE 1-continued

Vital Parameters and Liver-Function Tests in mice wild type (WT) or CB1 deficient after 4 Weeks of CCl4 Treatment

| Parameter | WT Olive oil | WT CCl4 | CB1−/− Olive oil | CB1−/− CCl4 |
|---|---|---|---|---|
| Aspartate transaminase (IU 1-1) | 94.7 ± 9.2 | 1887.2 ± 656.6* | 139.6 ± 24.3 | 1341.9 ± 457.1# |
| Alkaline phosphatase (IU 1-1) | 37.9 ± 5.9 | 55.0 ± 6.2* | 33.6 ± 2.0 | 56.4 ± 4.6# |
| Bilirubin Total | 3.5 ± 1.0 | 15.1 ± 4.2* | 3.6 ± 0.9 | 10.0 ± 3.4# |

Results are expressed as mean ± SEM.
*P < 0.05 vs WT olive oil;
P < 0.05 vs CB1−/− olive oil WT mice developed liver fibrosis after 4 weeks of treatment with CCl4, as shown by histologic analysis of liver tissue sections stained with PicroSirius red. The livers of CCl4-treated WT mice showed numerous septa formation with some nodules. Strikingly, CCl4-treated CB1−/− mice showed weaker fibrogenic response with reduced formation of fibrotic septa. Accordingly, the fibrosis score was significantly lower in CCl4-treated CB1−/− mice as compared to the CCl4-treated WT group (2.59±0.13 and 3.33±0.13 respectively, p<0.05). Moreover, hepatic collagen content, assessed by liver hydroxyproline determination, was strongly reduced by 40% in CCL4-treated CB1-deficient mice as compared to their WT counterparts (respectively 0.45±0.06 and 0.73±0.11 mg/mg of tissue (dry weight); p<0.05). Finally, necrosis and inflammation were not significantly different in CCl4-treated WT and CB1 −/− mice as shown in Table 2.

TABLE 2

Necrosis and inflammation in wild type (WT) and CB1−/− mice after 4 Weeks of CCl4 treatment

| Parameter | WT CCl4 | CB1−/− CCl4 |
|---|---|---|
| Necrosis | 1.3 ± 0.3 | 1.3 ± 0.2 |
| Inflammation | 1.4 ± 0.3 | 1.5 ± 0.2 |

Results are expressed as mean ± SEM.

Figure 1:
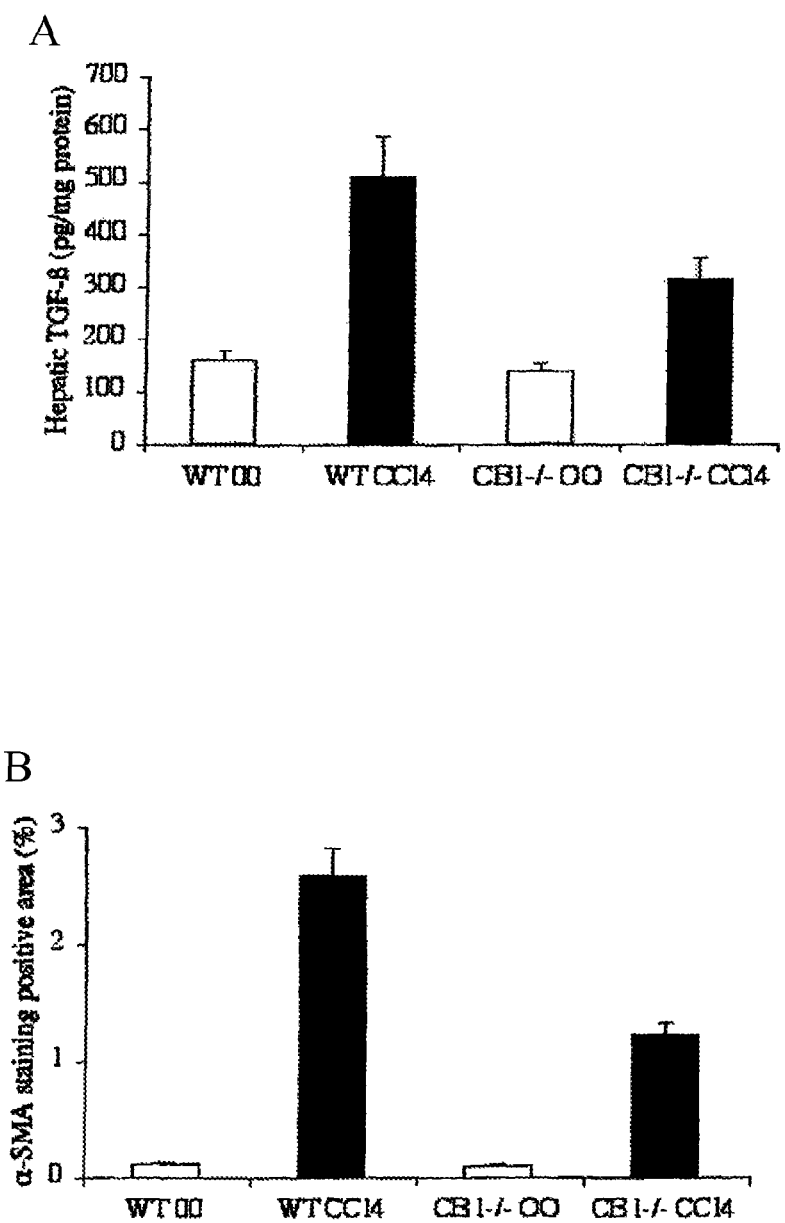
FIG. 1: Histogram showing hepatic TGFβ-1 content in pg per mg of soluble protein (panel A) and showing hepatic smooth muscle alpha actin expression as a percentage of total section surface area staining (panel B), both in wild type mice (shown as WT) and CB1 deficient mice (shown as CB1−/−). OO refers to the group of mice receiving only olive oil, while CCl4 shows the results for CCl4 intoxicated mice.

The hepatic content of the fibrogenic cytokine TGF-β1 was measured and the expression of smooth muscle α-actin was assessed, being a marker of hepatic myofibroblasts and of activated hepatic stellate cells. In CCl4-treated animals, production of TGF-β1 was reduced in CB1-deficient mice as compared to their wild type counterpart (FIG. 1A). In addition, smooth muscle α-actin was markedly attenuated in CCl4-treated CB1 −/− mice as compared to CCl4-treated WT animals (1.23±0.09 vs 2.58±0.23; p<0.05) (FIG. 1B).

Finally, in order to assess whether CB1 inactivation reduces hepatic myofibroblast accumulation by reducing their proliferation and/or apoptosis, hepatic myofibroblasts isolated from WT and CB1−/− mice were used. Serum deprivation was used as apoptotic stimuli. Serum deprivation hardly affected the viability of hepatic myfibroblasts isolated from wild type mice (WT) (FIG. 2). In contrast, serum starvation produced cytotoxic effects towards hepatic myfibroblasts isolated from CB1 −/− animals, as shown by cell rounding, shrinkage and detachment and reduction of viability (FIG. 2A). Serum deprivation also enhanced stimulation of caspase-3 like activity in CB1 −/− cells as compared to WT cells (FIG. 2B). Thus Hepatic myofibroblasts from CB 1 −/− mice show a higher apoptotic rate than cells from WT mice.

These results demonstrate that invalidation of CB1 receptor sensitizes hepatic myofibroblasts to apoptosis.

Example 3

Daily *Cannabis* Smoking is a Risk Factor for Fibrosis Progression in Chronic Hepatitis C 195 consecutive naïve patients with dated exposure (men/women: 140/55, aged 42±10) were included. Data collected were consumptions of *cannabis*, alcohol and tobacco during disease duration, age at contamination, gender, route of transmission, genotype, BMI, steatosis, activity and fibrosis (METAVIR), and fibrosis progression rate (median value being 0.08 per year).

By univariate analysis fibrosis progression rate superior to 0.08/year was associated to *cannabis* smoking as shown in table 3, alcohol intake greater or equal than 30 g/d (64%, p=0.03), moderate or marked steatosis (65%, p=0.004), age at contamination greater or equal than 25 (63%, p<0.01), and histological activity greater or equal than A2 (65%, p<0.001). In multivariate analysis, fibrosis progression rate >0.08 was independently related to daily *cannabis* smoking (OR=3.8; 95% CI (1.7-8.7)), alcohol intake greater or equal than 30 g/d (OR=2.1; 95% CI (1.0-4.6)), age at contamination greater or equal than 25 (OR=4.0; 95% CI (1.9-8.4)), and activity greater or equal than A2 (OR=7.5; 95% CI (3.5-16.1)). There is therefore a causal link between daily *cannabis* consumption and fibrosis progression.

TABLE 3

Incidence of Cannabis Consumption on Fibrosis progression

| Cannabis | Fibrosis progression rate superior to 0.08/year | p |
|---|---|---|
| None, n = 102 (52%) | 43 (42%) | |
| Occasional, n = 30 (16%) | 15 (50%) | 0.029 |
| Daily, n = 63 (32%) | 40 (63%) | |

Example 4

Hepatic Myofibroblast Cultures in the Presence of CB1 Receptor Antagonists

Isolation and Culture of Human Hepatic Myofibroblasts.

Human hepatic myofibroblasts were obtained by outgrowth of explants prepared from surgical specimens of normal liver obtained from surgery of benign or malignant liver tumors, as previously described. This procedure was performed in accordance with ethical regulations imposed by the French legislation. Cells were cultured in Dulbecco's modified Eagle's medium (DMEM) containing 10% serum (5% fetal calf serum, and 5% human serum, DMEM 5/5) and were used between the third and seventh passage. Experiments were performed on cells that were made quiescent by a 48 h incubation in serum-free Waymouth medium unless otherwise indicated.

Isolation and Culture of Mice Hepatic Myofibroblasts.

Mice myofibroblasts were isolated by collagenase perfusion and purified by density gradient in Nicodenz, as described. After isolation, cells were cultured in DMEM medium containing 20% fetal calf serum. At day one, cell debris and non-adherent cells were removed by washing, and the cells were further cultured in DMEM medium containing 10% FCS. Cells were used between the third and ninth passage.

Apoptosis Assays.

Apoptosis assays were performed on non-confluent cells allowed to attach overnight in DMEM 5/5 and serum-starved for 48 h, as described in Davaille J et al., *J Biol Chem* 2002; 277:37323-30, and Li L et al., *J Biol Chem* 2001; 276:38152-8. Nuclear morphology was assayed using DAPI staining, caspase-3-like activity was assayed on cell lysates using AC-DEVD-AFC as substrate, and DNA laddering was assayed by agarose gel electrophoresis of total DNA extracted using an Apoptotic DNA Ladder Kit.

Cell Viability.

Cells (7,000 cells/well in 96-well plates) were allowed to attach overnight in DMEM5/5, serum-starved for 48 h in DMEM without phenol red and treated with the indicated effectors for 16 h. CellTiter 96 AQueous One Solution reagent was added to each well and absorbance was recorded at 490 nm.

DNA Synthesis Measurement.

DNA synthesis was measured in triplicate wells by incorporation of [3H] thymidine, as previously described (Tao, J., et al., J Biol Chem, 1999. 274(34): p. 23761-23769). Confluent human hepatic myfibroblasts were serum-starved for 48 h and further stimulated for 30 h with 20 ng/ml PDGF-BB. Confluent mice hepatic myfibroblasts were serum-starved for 24 h in the presence of 0.1% BSA, and further stimulated for 30 h with 20 ng/ml PDGF-BB in the presence of 0.01% BSA. [3H] thymidine (0.5 µCi/well) was added during the last 20 h of incubation.

The cell culture was performed as described in example 1 herein. Cell culture of both human and mouse hepatic myofibroblasts were exposed to increasing doses of CB1 receptor antagonist SR141716 and the DNA synthesis of hepatic myofibroblasts was measured.

In human hepatic myofibroblasts, SR 141716 dose-dependently inhibited DNA synthesis elicited by 20 ng/ml PDGF-BB (FIG. 3A), with a half maximal inhibition occurring in the presence of 300-400 nM of the compound.

SR141716 also inhibited DNA synthesis elicited by 20 ng/ml PDGF-BB in murine myofibroblasts isolated from wild type mice, whereas, it only marginally affected proliferation of CB1-/- cells (FIG. 3B).

These results demonstrate that the CB1 antagonist SR141716 causes growth inhibition of human and mice hepatic myofibroblasts and is acting through CB1 receptors.

Example 5

Assessment of the Therapeutic Effect of SR 141716 on Induced Liver Fibrosis

The antifibrogenic potential of the CB1 antagonist SR 141716 in an experimental model of liver fibrosis, induced by chronic intoxication with carbon tetrachloride was evaluated.

Drug Administration

SR 141716 (10 mg/kg body weight) was dissolved freshly before use, in a vehicle solution (2 drops of Tween 80 in 10 ml of PBS containing 10% dimethylsulfoxide and 5% ethanol) and sonicated.

Animals and Experimental Design.

CD1 mice were obtained from Janvier (France). All experiments were performed using accepted ethical guidelines. 36 males, aged 10-12 weeks, were used and animals were divided into the following groups: vehicle-treated, olive oil group (n=3); vehicle-treated, CCl4 group (n=14); SR 141716-treated olive oil group (n=3); SR 141716A-treated, CCl4 group (n=16). Animals were housed in temperature and humidity controlled rooms, kept on a 12-h light/dark cycle and provided unrestricted amounts of food and water, unless otherwise specified. Fibrosis was induced by giving carbon tetrachloride ($CCl_4$) (Sigma, St Quentin-Fallavier, France) mixed with olive oil (1 vol:10 vol) at 0.5 ml/kg body weight, by intra peritoneal injection, twice a week for one month. SR141716 or vehicle was administered daily by intraperitoneal injection. Treatment was started 7 days before carbon tetrachloride ($CCl_4$) injection and lasted throughout the $CCl_4$ treatment.

Coadministration of $CCl_4$ with vehicle (PBS containing 10% DMSO, 5% ethanol, 0.1% Tween 80) elicited massive death of the animals reaching 50% of the population after one month (see FIG. 4). In contrast, coadministration of mice with $CCl_4$ together with 10 mg/kg SR 141716 was associated with a higher survival rate at one month (83%). There were no deaths in sham animals, whether treated with SR141716 or vehicle.

Therefore, these results indicate a hepatoprotective role for the CB1 antagonist SR141716.

Example 6

Assessment of an Optimal Regimen for Oral Administration of SR141716 in the Treatment of Liver Fibrosis In order to define optimal conditions of long term treatment with SR141716 the following is performed.

40 male CD1 mice are divided into the following groups: sham (olive oil n=3); CCl4 (n=12); SR 141716-treated sham group (olive oil n=3); 2 groups of SR 141716-treated CCl4 group (n=2 times 12). Animals are housed in temperature and humidity controlled rooms, kept on a 12-h light/dark cycle and provided unrestricted amounts of food and water, unless otherwise specified. Fibrosis is induced by giving carbon tetrachloride (CCl4) (Sigma, St Quentin-Fallavier, France) mixed with olive oil (1 vol:10 vol) at 0.5 ml/kg body weight, by intra peritoneal injection (IP), twice a week. Sham animals for CCl4 receive olive oil. SR 14 1716 is included in RM1 mice food (DIETEX, France) at a concentration of 65 mg/kg, is given to the SR141716 treated group. On the assumption that a mouse weighing 30 g will eat 5 g per day, the final expected dose of SR 141716 administered is 10 mg/kg. SR 141716 treatment starts either 7 days before carbon tetrachloride (CCl4) injection (12 mice), or starts 7 days after the first injection (12 mice), and lasts throughout the CCl4 treatment. After 5 weeks, the animals are starved overnight and killed 48 h after the last CCl4 injection. Liver samples are taken from several lobes and either i) snap-frozen in liquid nitrogen and homogenized in RNA extraction solution, ii) homogenized in H2O and snap frozen in liquid nitrogen for hydroxyproline determination or iii) fixed in buffered formalin. Snap frozen sample will be stored at −80° C. until use. Blood samples are also collected in siliconed tubes containing inert gel barrier and clot activator disc (Venoject, Terumo, France), serum separated by centrifugation and stored at −20° C. until use.

The results are used in order to assess the concentration at which toxicity is therapeutically acceptable.

The invention claimed is:

1. A method of reducing hepatic fibrosis in a mammal in need thereof which comprises administering a therapeutically effective amount of at least one CB1 receptor antagonist.

* * * * *